United States Patent
Lawrence

[11] Patent Number: 6,048,354
[45] Date of Patent: Apr. 11, 2000

[54] SLIDING KNIFE AND NEEDLE ASSEMBLY FOR MAKING A PORTAL FOR ENDOSCOPIC OR ARTHROSCOPIC SURGERY

[76] Inventor: Jeffrey M. Lawrence, Rte. 4, Box 81B, Viroqua, Wis. 54665

[21] Appl. No.: 09/241,887

[22] Filed: Feb. 1, 1999

[51] Int. Cl.[7] .................................................. A61B 17/34
[52] U.S. Cl. .......................................... 606/185; 606/167
[58] Field of Search ................................... 606/167, 170, 606/171, 181, 184, 185; 30/151, 2

[56] References Cited

U.S. PATENT DOCUMENTS

| | | |
|---|---|---|
| 4,203,444 | 5/1980 | Bonnell et al. . |
| 4,614,187 | 9/1986 | Mulhollan et al. . |
| 4,790,312 | 12/1988 | Capuano et al. . |
| 5,084,058 | 1/1992 | Li . |
| 5,120,318 | 6/1992 | Nallapareddy . |
| 5,356,419 | 10/1994 | Chow . |
| 5,571,127 | 11/1996 | DeCampli ............................... 606/167 |
| 5,599,351 | 2/1997 | Haber et al. ............................... 30/151 |
| 5,908,432 | 6/1999 | Pan .......................................... 606/167 |

*Primary Examiner*—Michael Buiz
*Assistant Examiner*—Kevin Truong

[57] ABSTRACT

A sliding knife and needle assembly for creating a percutaneous incision or portal in a living body comprises an elongate hollow rectangular handle having a closed first end, an open second end and a slot extending along one side, with the handle defining a first central longitudinal axis. A knife blade and introducer assembly is slidably housed inside the handle for sliding along the axis. The knife blade is substantially flat and rigidly attached to one end of the introducer. The introducer has a longitudinal bore which extends along a second axis parallel to the first axis. A locking button is attached to the introducer and extends through the slot in the handle. A needle is affixed to the first end of the handle and extends through the second axis and beyond the second end of the handle. The needle extends through the bore in the introducer. By this construction, the knife blade and introducer can be slid into and out of the handle along the first axis and locked in a retracted position wherein the knife blade is enclosed by the handle and slid to an extended position wherein the knife blade extends from and beyond the second end of the handle by releasing the locking button and sliding it along the slot.

20 Claims, 3 Drawing Sheets

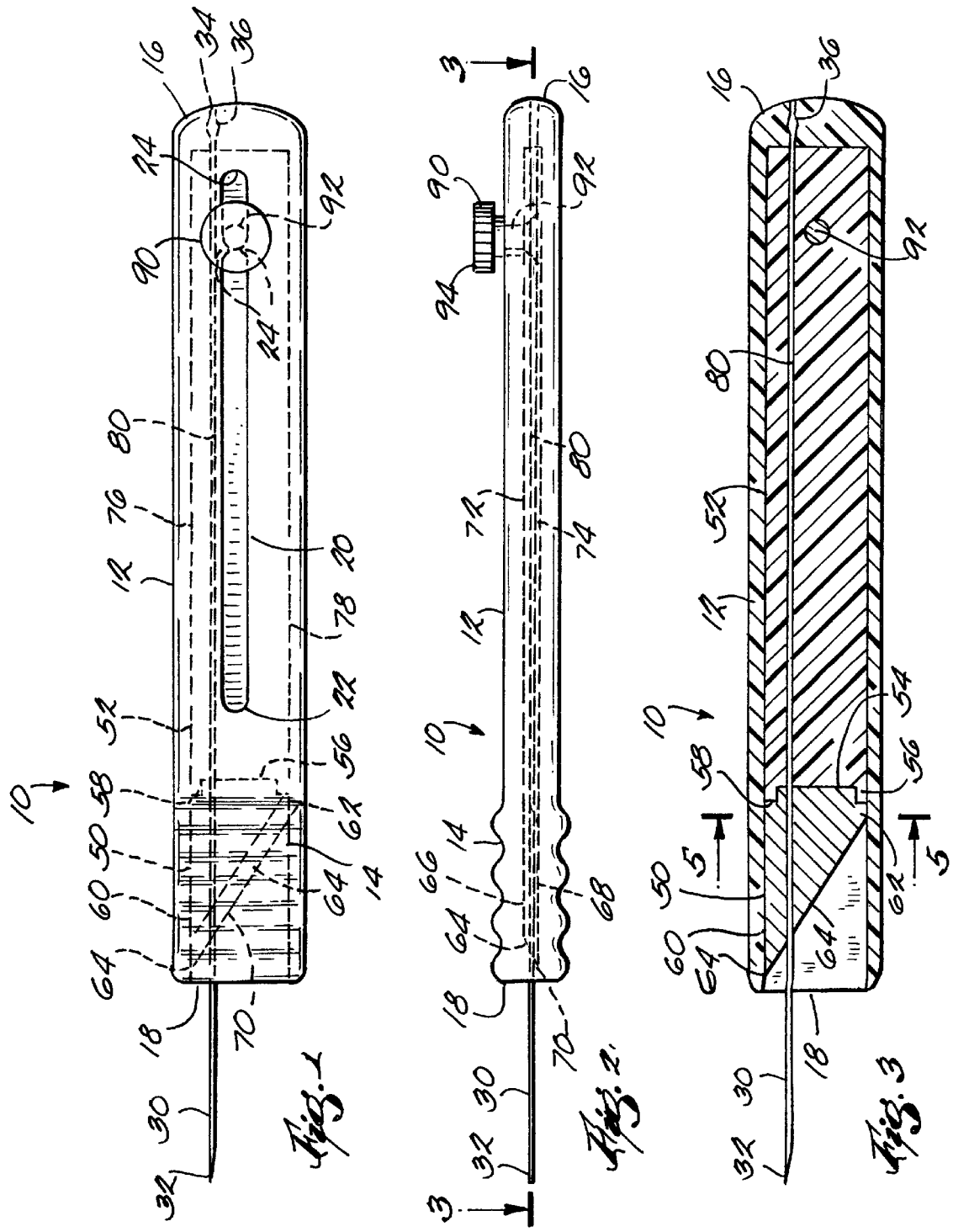

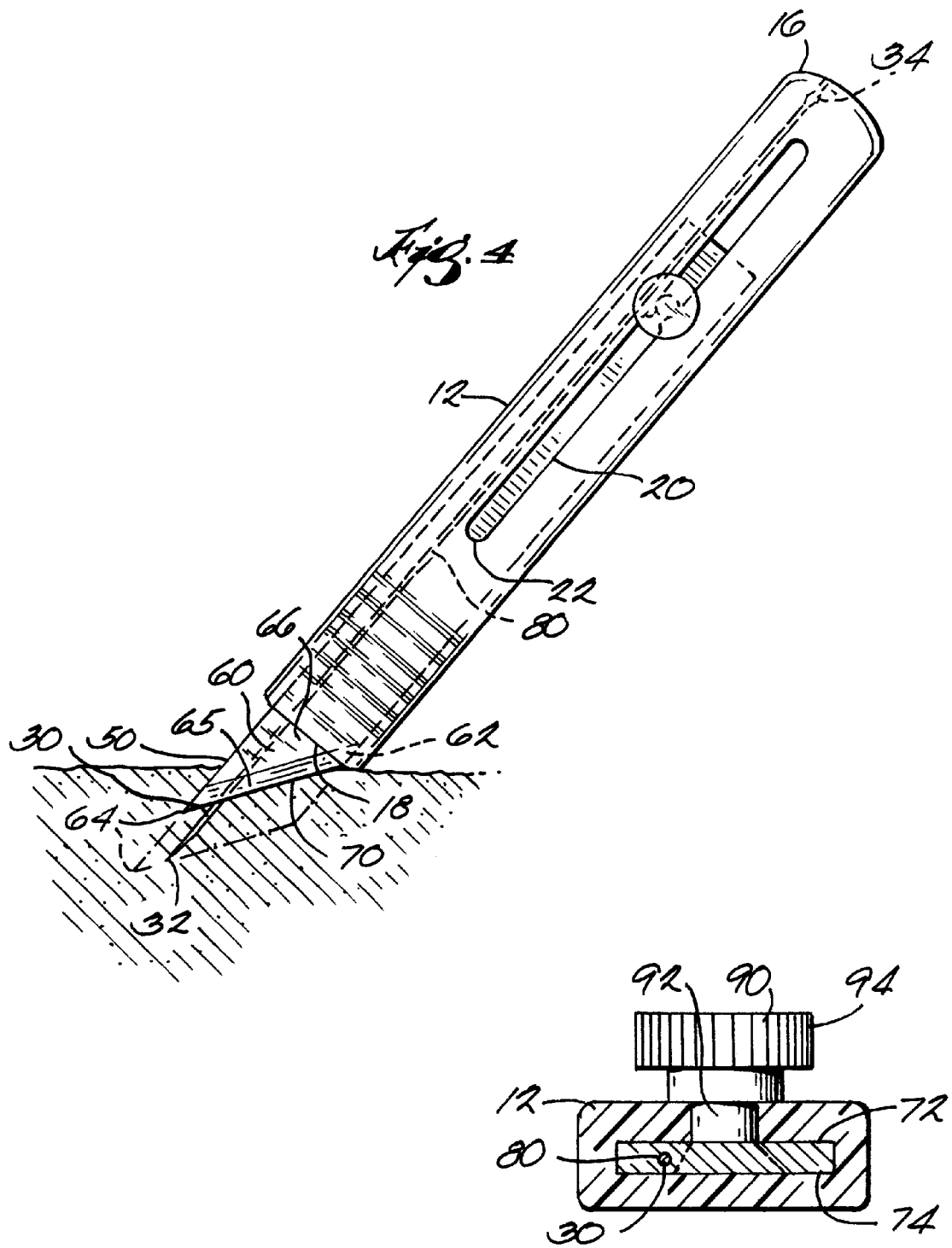

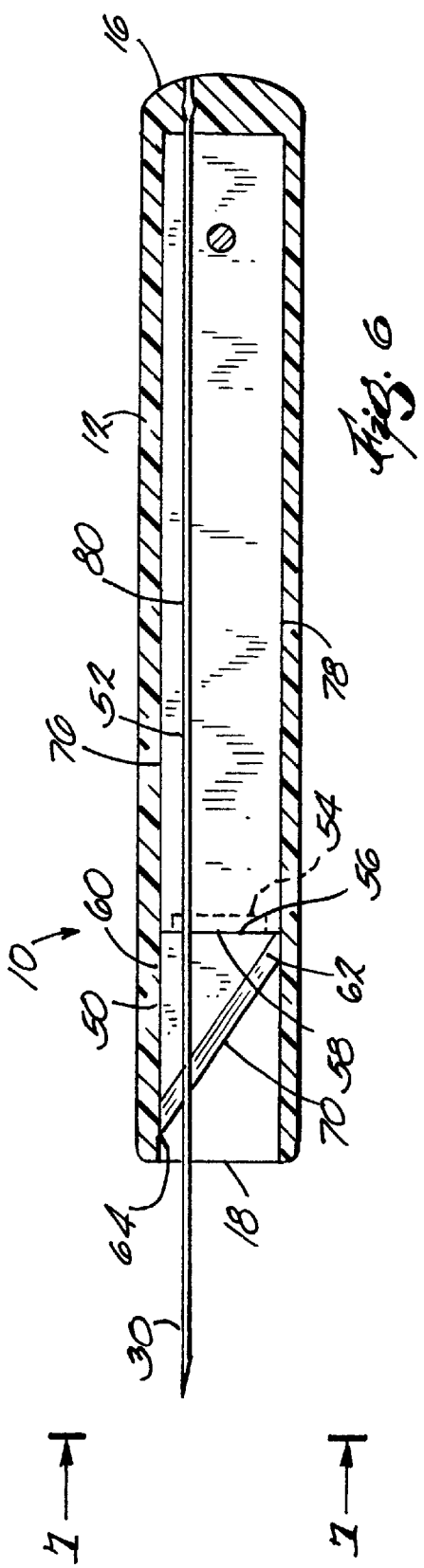
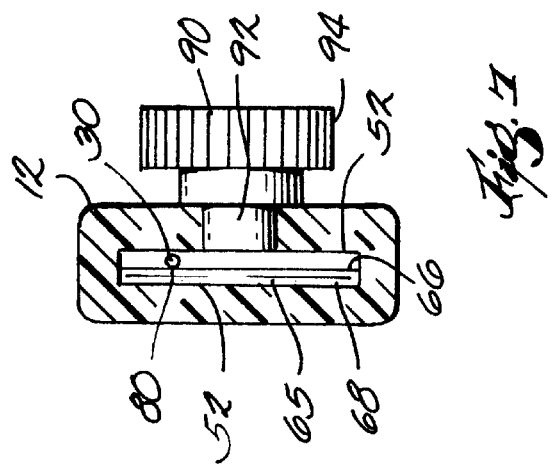

6,048,354

SLIDING KNIFE AND NEEDLE ASSEMBLY FOR MAKING A PORTAL FOR ENDOSCOPIC OR ARTHROSCOPIC SURGERY

FIELD OF THE INVENTION

The invention relates to surgical instruments, more particularly to an arthroscopy or endoscopy portal maker. The invention comprises an apparatus and method that will provide a very accurate percutaneous incision in a living body for creating a portal for arthroscopic or endoscopic surgery.

BACKGROUND OF THE INVENTION

The invention relates to a device for the creation of a precise working portal for arthroscopic surgery, endoscopic surgery or other surgical procedures using the aid of video technology to visualize internal anatomical structures. As minimally invasive surgery has evolved, numerous tools have been developed to assist in treating medical conditions that have previously been treated with open and more invasive techniques. Arthroscopic surgery of the knee is a common example of this surgery. Typically, the first step in arthroscopic surgery is to create a portal for the camera. This "blind" portal is made by palpating known anatomical structures near the desired location of the portal and making an incision. The camera is placed through this portal and the knee is inflated with fluid. Typically, next a spinal needle is percutaneously directed toward the area of pathology to identify the correct location of a "working" portal. The working portal will provide access for future instruments to be passed. A knife blade is then passed into the joint to approximate the plane of the needle. This approximation can lead to several problems. The knife can pass on a different plane, causing injury to vital structures. The knife blade can pass in a different plane, making placements of instruments difficult. Finally, if the knife blade does not pass completely into the joint, it can leave a tighter working portal which makes passing instruments more difficult as they get caught up in fat and synovium that lines the joint.

Other persons have attempted to design devices that would create an accurate portal. For example, U.S. Pat. No. 5,120,318 discloses a portal maker with a puncturing tool and a cannulated shaft having a circular cross section. The puncturing tool is hollow so it can accept a wire rod passing inside of it during one step of a disclosed procedure. U.S. Pat. No. 4,790,312 discloses a surgical instrument for operating percutaneously in a living body. It has a hollow handle and a an elongated shaft of circular cross section.

There is no single surgical instrument in the prior art that is able to successfully and accurately identify the proper location for and then make an unlined working portal in that exact location in a living being for preparation of arthroscopic or endoscopic surgery.

SUMMARY OF THE INVENTION

A sliding knife and needle assembly for creating a percutaneous incision or portal in a living body is disclosed. It comprises an elongate hollow rectangular handle having a closed first end, an open second end and a slot extending along one side, with the handle defining a first central longitudinal axis. A knife blade and introducer assembly is slidably housed inside the handle for sliding along the axis. The knife blade is substantially flat and rigidly attached to one end of the introducer. The introducer has a longitudinal bore which extends along a second axis parallel to the first axis. A locking button is attached to the introducer and extends through the slot in the handle. A needle is affixed to the first end of the handle and extends through the second axis and beyond the second end of the handle. The needle extends through the bore in the introducer. By this construction, the knife blade and introducer can be slid into and out of the handle along the first axis and locked in a retracted position wherein the knife blade is enclosed by the handle and slid to an extended position wherein the knife blade extends from and beyond the second end of the handle by releasing the locking button and sliding it along the slot.

In one embodiment, the needle is solid, preferably 18 to 22 gauge and has a first end affixed to the first end of the handle and a sharp second end that can be inserted through the skin and muscle of the living body.

Preferably, the handle is made of plastic and has a gripping surface on the outside proximate one end. The knife blade has an elongate cutting surface set at an angle with respect to the first axis. Accordingly, the cutting face has a cutting tip at one end. In one embodiment, the knife blade also has a bore coaxial with the bore in the introducer and along the second axis, and the knife blade bore extends through the angled cutting face near the tip. Preferably the locking button also retains the knife blade and introducer from sliding too far beyond the second end of the handle.

The invention also provides a needle and knife assembly for creating a portal for arthroscopic or endoscopic surgery comprising an elongate solid central needle having a second sharp free end and a first fixed end, and a substantially straight angled knife blade having an angled cutting end and a rear end. An introducer is affixed to the rear end of the knife blade and has a longitudinal bore through which the needle extends, with the bore sized so that the knife blade and the introducer are free to slide along the needle. A locking button is affixed to the introducer. An elongate hollow handle partially envelopes the knife blade and the introducer and has a first solid end to which said first fixed end of the needle is attached, a second open end and a slot along one side. The knife blade and the introducer are free to slide from a retracted position wholly inside the handle wherein only the needle protrudes from the first end of the handle to an extended position wherein the knife blade extends beyond the second end of the handle and is proximate the second end of the needle by releasing the locking button and sliding it along the slot.

In one embodiment, the needle and the bore in the introducer define a second axis, the centerline of the elongate hollow handle defines a first axis and the first axis and second axis are parallel. The handle may be either rectangular or cylindrical in shape.

The invention also provides a method of making a portal in a living body for arthroscopic or endoscopic surgery comprising slidingly positioning an angled flat knife blade and an elongated cannulated introducer into the hollow interior of an elongate handle, with the handle having a first open end and a second closed end and a slot extending along one side. The handle also has a needle with a sharp end extending outwardly from the first end, with the needle permanently affixed to the second end of the handle. The needle defines a longitudinal axis through the handle. The needle also extends through a bore in the cannulated introducer. The skin and muscle of the living body are punctured with the sharp end of the needle and the sharp end of the needle is inserted into the body at a desired location. Next, the knife blade and the introducer are slid along the longitudinal axis to an extended position whereby the knife blade creates a percutaneous incision in this skin and muscle proximate the needle by grasping and manipulating the locking button attached to the introducer. Finally, the surgeon simultaneously withdrawals the needle and the knife blade from the incision whereby an accurate portal is left in the body near the location at which the end of the needle has been inserted.

It is an object of the invention to provide a single surgical tool and method that will locate the proper location for an arthroscopic portal and also create a percutaneous incision at that location.

Further objects of the invention will be appreciated by review of the preferred embodiment and claims of the invention.

BRIEF DESCRIPTION OF THE DRAWINGS

FIG. 1 is a top view of the invention;

FIG. 2 is a side view of the invention;

FIG. 3 is a cross sectional view of one preferred embodiment taken along line 3—3 of FIG. 2;

FIG. 4 is a side view of the invention as it is creating a portal;

FIG. 5 is a cross sectional view taken along 5—5 of FIG. 3;

FIG. 6 is cross sectional view of a second preferred embodiment of the invention;

FIG. 7 is a cross sectional view taken along 7—7 of FIG. 6.

Other principal features and advantages of the invention will become apparent to those skilled in the art on review of the following drawings, the detailed description and the claims.

DESCRIPTION OF A PREFERRED EMBODIMENT

Before explaining at least one embodiment of the invention in detail, it is to be understood that the invention is not limited in its application to the details of construction and the arrangement of the components set forth in the following description or illustrated in the drawings. Other embodiments may be used to implement the invention, and the invention may be used in other environments.

The present invention, as described herein and seen in the Figures, provides an apparatus 10 and method to locate and provide an accurate portal, especially a working portal, for preparation of arthroscopic or endoscopic surgery. The knife blade 50 for making the incision is capable of sliding out of a handle 12 and along the axis of a needle 30 to accurately place the incision at the location of the needle. In use, the knife blade 50 starts in a retracted position, as seen in FIG. 1. During the surgical procedure, the knife blade 50 is ultimately slid to an extended position wherein the cutting face 64 of the knife blade is proximate the distal end 32 of the needle 30. FIG. 4 is an example of the knife blade at an intermediate location in the procedure.

In the retracted position, the outside or exterior of the sliding knife and needle assembly 10 primarily comprises a hollow housing case or handle 12 with a needle 30 extending from one end. The handle 12 is approximately 6 to 8 centimeters long and can be either rectangular or cylindrical in shape. The shape is optimized to be appropriate for a surgeon's hand. On the exterior of the handle can be gripping bumps or knurling 14 to aid in grasping the handle.

Preferably the handle is molded from relatively stiff, tough plastic. The longitudinal centerline of the handle defines a first axis (not shown).

The handle 12 has a solid first rear end 16 and an open second end 18. Along one side of the handle 12 is an open longitudinal slot 20. The slot extends for approximately 4–6 centimeters from near the closed first end 16, most of the way along one side of the handle toward the open second end 18. The slot has an end wall 22 near the second end 18 and an end wall 24 near the first end 16 of the handle. In one embodiment, the slot also has a pair of nubs or protrusions 24 molded into the slot near the first end of the handle for capturing the post 92 of the locking button 90 between the protrusions and the end wall 24 near the closed end of the handle.

In the retracted position, stored inside the handle 12, are the knife blade 50 and introducer 52. The knife blade 50 and introducer 52 are attached to each other so as to make a single rigid piece. In a preferred embodiment, the knife blade 50 has a tail section 54 which is inserted into a complementary opening in the front end of the introducer and the introducer is molded onto or otherwise adhered to the knife blade in a manner that is known in the art.

In one embodiment, the knife blade 50 is a #11 surgical blade and is generally trapezoidal in shape with a base wall 56 that is parallel to the wall 58 at the distal end of the introducer 52. The knife blade has first 60 and second 62 parallel side walls and a cutting face 65 which is angled with respect to the centerline of the handle extending between the side walls. The cutting face terminates in a tip 64 at the junction of the cutting face 65 and the first side wall 60. The knife blade 50 also has a top wall 66 and a bottom wall 68. In one embodiment, the cutting face 65 is ground from the top wall to the bottom wall so that it has a cutting line 70 along the distal end of the bottom wall 68 along its entire face. In another embodiment, the knife blade is ground oppositely, so the cutting line 70 is at the very distal end of the top wall (See FIGS. 6 and 7).

Immediately behind the knife blade 50 and rigidly attached thereto is the introducer 52. The introducer is made of plastic and is sized to slide within the hollow handle along with the knife blade 50. Preferably the introducer is elongate and rectangular with top 72 and bottom 74 parallel walls and first 76 and second 78 parallel side walls which also are aligned with the first 60 and second 62 side walls of the knife blade. The top, bottom and side walls of the introducer slidingly fit against complementary walls within the hollow handle.

Approximately one quarter of the distance between the first 76 and second 78 parallel side walls of the introducer is a longitudinal bore 80 extending through the introducer 52. The bore is parallel to the longitudinal centerline of the handle upon which the knife blade and introducer slide and defines a second axis. Positioned in the bore 80 is the needle 30. The bore 80 is sized so the knife blade 50 and introducer 52 slide over the needle 30 as they are moved from the retracted to an extended position.

In a preferred embodiment, the needle 30 is approximately 10 to 12 cm long. It is optimally 18 to 22 gauge with a sharpened distal end 32 and a blunt proximal end 34. The proximal end may preferably have a retaining bulb 36 for retaining the needle in the solid first end 16 of the handle 12. The needle extends along the second axis longitudinally through the handle, and the distal end 32 extends beyond the first open end 18 of the handle by approximately 2 to 6 cm.

In one embodiment, as seen in FIGS. 6 and 7, the introducer 52 is thicker than the knife blade 50. The bore 80 is offset from the knife blade 50 and terminates at the junction of the knife blade and the introducer 52. The needle 30 lies immediately above the top wall of the knife blade. In another embodiment, the knife blade 50 also has a bore 82 coaxial with the bore 80 extending through the introducer. The bore 82 has a distal end 84 which lies in the knife blade cutting face 65. The needle also extends through the bore 82 in the cannulated knife blade and the distal end 84.

On the top wall 72 of the introducer 52 is a locking button 90 which extends through the slot 20 in the handle 12. The locking button 90 has a post portion 92 and a head portion 94 which extends laterally over the side of the handle 12 adjacent the slot 20. In one embodiment, the post 92 of the locking button 90 is retained behind the two protrusions 24 on the sides of the slot 20 to retain the knife blade 50 and introducer 52 in the retracted position in the handle. In an alternative embodiment, the head 94 may screw onto the post 92 to capture the side of the handle by the slot 20 between the bottom of the head 94 and the top wall 72 of the introducer. In another embodiment, the locking button 90 may move transversely into and out of a transverse slot in the handle near its first end 16 for lockingly retaining the introducer 52 and knife blade 50.

The locking button 90 serves two purposes. First, it maintains the knife blade 50 and introducer 52 in the handle as the handle is initially used to puncture the skin and muscle with the needle and locate the distal end of the needle at the desired location. When the needle 30 is positioned at the correct location by the surgeon, the locking button is pushed manually to release the lock. Next, it is pushed longitudinally along the slot in the handle so the knife blade 50 and introducer 52 slide along the inside of the handle and the needle to an extended position whereby the knife blade makes an accurate incision in the living body immediately adjacent the needle (see FIG. 4). In a final step of the method, the knife blade and needle are removed from the portal, preferably simultaneously. The handle and locking button are both grasped and pulled outwardly so that a percutaneous incision is left at the precise location identified by the needle. Other arthroscopic instruments can now be inserted into the portal.

The invention is capable of other embodiments and for being practiced or carried out in various ways, and it should be understood that the preferred embodiments are but two of many embodiments. Also, it is to be understood that the phraseology and terminology employed herein is for the purposes of description and should not be regarded as limiting.

I claim:

1. A knife assembly for creating a percutaneous incision in a living body comprising;
    a. An elongate hollow rectangular handle having a closed first end, an open second end and a slot extending along one side, said handle defining a first longitudinal central axis,
    b. A knife blade and introducer assembly slidably housed in said handle for sliding along said first axis, said knife blade being substantially flat and rigidly attached to one end of said introducer, said introducer having a longitudinal bore which extends along a second axis parallel to said first axis,
    c. A locking button attached to said introducer and extending through said slot in said handle and,
    d. A needle affixed to said first end of said handle extending through said handle along said second axis and beyond said second end of said handle and also extending through said longitudinal bore of said introducer, whereby said knife blade and said introducer can be slid into and out of said handle along said first axis and locked in a retracted position wherein said knife blade is enclosed by said handle and slid to an extended position wherein said knife blade extends from and beyond said second end of said handle by releasing said locking button and sliding it along said slot.

2. The knife assembly of claim 1 wherein said needle is solid and has a first end and a second end with said first end affixed to said first end of said handle and said second end being sharpened for insertion into and through the skin and muscle of the living body.

3. The knife assembly of claim 2 wherein said needle is 18 to 22 gauge.

4. The knife assembly of claim 1 wherein said handle is made of plastic and is approximately 6–8 centimeters long.

5. The knife assembly of claim 1 wherein said handle has a knurled gripping surface on the sides near said second end.

6. The knife assembly of claim 5 wherein said knife blade has an elongate cutting face which is set at an angle with respect to said first axis.

7. The knife assembly of claim 6 wherein said cutting face has a cutting tip at one end of said cutting face.

8. The knife assembly of claim 7 wherein said knife blade also has a bore coaxial with said bore of said introducer along said second axis and said knife blade bore extends through said angled cutting face near said tip.

9. The knife assembly of claim 8 wherein said cutting face is also angled from the topside of the knife blade to the bottom side and is also angled through said bore.

10. The knife assembly of claim 1 wherein said slot has a first end proximate the first end of said handle and a second end and said locking button also acts to retain the knife blade and introducer by contacting said second end of said slot to keep said knife blade and said introducer from passing through and beyond the second end of said handle.

11. A knife assembly for use in creating a portal for arthroscopic or endoscopic surgery comprising:
    a. An elongate solid central needle having a second sharp free end and a first fixed end,
    b. A substantially straight angled knife blade having an angled cutting end, and a rear end,
    c. An introducer affixed to said rear end of said knife blade and having a longitudinal bore through which said needle extends, with the bore sized so that said knife blade and said introducer are free to slide along said needle,
    d. A locking button affixed to said introducer, and
    e. An elongate hollow handle partially enveloping said knife blade and said introducer and having a first solid end to which said first fixed end of said needle is attached, a second open end and a slot along one side, whereby said knife blade and introducer are free to slide from a retracted position wholly inside said handle wherein only said needle protrudes from said first end of said handle to an extended position wherein said knife blade extends beyond said second end of said handle and is proximate the second end of the needle by the releasing said locking button and sliding it along said slot.

12. The knife assembly of claim 11 wherein said needle is 18 to 22 gauge and approximately 12–16 centimeters long.

13. The knife assembly of claim 11 wherein said needle and said bore in said introducer define a second axis and the centerline of said elongate hollow handle defines a first axis and said first axis and said second axis are parallel.

14. The knife assembly of claim 13 wherein said first axis and said second axis are collinear.

15. The knife assembly of claim 11 wherein said handle is cylindrical.

16. The knife assembly of claim 11 wherein said handle is rectangular.

17. The knife assembly of claim 11 wherein said handle has a gripping means on the outer surface proximate said second end.

18. The knife assembly of claim 11 wherein the interior surface of said handle and the outer surface of said introducer have complementary shapes to guide said introducer and said knife blade as they are slid along the inside of the handle.

19. The knife assembly of claim 11 wherein said knife blade also has a longitudinal bore on said second axis and said needle extends through said knife blade bore.

20. A method of making a portal in a living body for arthroscopic or endoscopic surgery comprising:

a. Slidably positioning an angled flat knife blade and an elongate cannulated introducer into the hollow interior of an elongate handle, said handle having a first open end, a second closed end and a slot extending along one side, said handle also having a needle with a sharp end extending outwardly from said first end, said needle permanently affixed to said second end of said handle, said needle defining a longitudinal axis through said handle, said needle also extending through a bore in the cannulated introducer, b. Puncturing the skin and muscle of the living body with the sharp end of the needle and inserting the needle at a desired location, c. Sliding said knife blade and said introducer along said longitudinal axis to an extended position so that the knife blade creates a percutaneous incision in the skin and muscle proximate said needle by grasping and manipulating the locking button, d. Simultaneously withdrawing the needle and knife blade from the incision, whereby an accurate portal is left in the body near the location at which the end of the needle had been inserted.

* * * * *